United States Patent [19]

Carpenter et al.

[11] 3,996,268
[45] Dec. 7, 1976

[54] CROSS-LINKING REAGENT FOR INSULIN SYNTHESIS

[75] Inventors: Frederick H. Carpenter; Wolf-Dieter Busse, both of Berkeley, Calif.

[73] Assignee: The Regents of the University of California, Berkeley, Calif.

[22] Filed: Sept. 3, 1974

[21] Appl. No.: 502,425

[52] U.S. Cl. .................. 260/479 S; 260/326.4; 260/471 A; 260/544 F; 260/544 Y; 260/546

[51] Int. Cl.$^2$ .......... C07C 103/147; C07C 103/183; C07C 149/20

[58] Field of Search ...................... 260/479 S

[56] References Cited

UNITED STATES PATENTS 3,330,857   7/1967   Hess .............................. 260/479 S

OTHER PUBLICATIONS

Fieser et al., Reagents for Organic Synthesis, vol. 1 (1967), pp. 842, 1196.
Bodansky et al., J. Amer. Chem. Soc., vol. 81 (1959), pp. 5688–5691.
Schwartz et al., J. Amer. Chem. Soc., vol. 81 (1959), pp. 5691–5695.

*Primary Examiner*—Jane S. Myers
*Attorney, Agent, or Firm*—Phillips, Moore, Weissenberger, Lempio & Strabala

[57] ABSTRACT

Carbonyl-bis (L-methionine p-nitrophenyl ester) and its analogues are useful reagents for the intermolecular cross-linking of two chain peptide molecules such as occur in the hormone insulin. The cross-linking occurs across amino groups at preferred positions in the two peptide chains to fix the relative spacial position of the peptide chains and permit the oxidative formation of necessary disulfide bridges between the chains in high yields. The reagent is then removed from the linked chains to yield the insulin molecule. A method for preparation of the reagent is disclosed. Further, a procedure is disclosed by which the cross-linking reagent is used to specifically block certain amino groups on insulin to yield a cross-linked insulin which in turn is used to prepare isotopically labeled insulin and insulin analogues.

4 Claims, No Drawings

CROSS-LINKING REAGENT FOR INSULIN SYNTHESIS

BACKGROUND OF THE INVENTION

The invention described herein was made in the performance of work under research grants from the United States Public Health Service.

Diabetes mellitus is a disease which has afflicted humans since the beginning of recorded history. Despite increased knowledge of the disease today there is still no cure for the illness. A great step forward in control of the disease was made by Banting and Best in the early 1920's when they reported successful treatment of the symptoms by injection of partially purified extracts of pancreas. These extracts were subsequently shown to contain the hormone, insulin. Today, the symptoms of the disease can be largely controlled for long periods of time by daily injection of the purified hormone.

At the present time sufficient insulin appears to be available from slaughter-house animals to supply the needs of the developed countries. Whether this will remain true when all the world's people become available for insulin therapy is questionable. The availability of insulin is closely related to the world food supply which in turn determines the amount of animal production. This may not be sufficient to supply the demands of the world population. The need for a practical synthesis of insulin is therefore obvious. Another factor influencing the need for a practical synthesis of insulin is the desirability of using a drug that is similar if not identical, to the human hormone since the animal derived insulins normally used in therapy differ in some molecular respects from human insulin. Administration of products which are not identical may elicit immunological and other side reactions which detract from the therapy. Although pork insulin is quite similar to human insulin it is not identical. Even so, there is not enough pork insulin to supply the demands of the medical profession and as a consequence the less desirable beef insulin (or mixtures of pork and beef) is the predominant commercial product.

All insulins, regardless of species of origin, are made up of two peptide chains (denoted A and B chains) which are connected together through two disulfide bridges. The human insulin molecule may be schematically represented by the following linear formula:

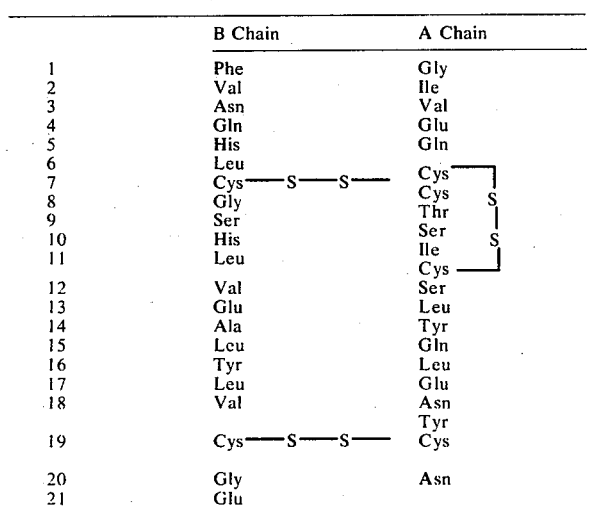

|    | B Chain | A Chain |
|----|---------|---------|
| 1  | Phe     | Gly     |
| 2  | Val     | Ile     |
| 3  | Asn     | Val     |
| 4  | Gln     | Glu     |
| 5  | His     | Gln     |
| 6  | Leu     | Cys     |
| 7  | Cys—S—S— | Cys    |
| 8  | Gly     | Thr     |
| 9  | Ser     | Ser     |
| 10 | His     | Ile     |
| 11 | Leu     | Cys     |
| 12 | Val     | Ser     |
| 13 | Glu     | Leu     |
| 14 | Ala     | Tyr     |
| 15 | Leu     | Gln     |
| 16 | Tyr     | Leu     |
| 17 | Leu     | Glu     |
| 18 | Val     | Asn     |
|    |         | Tyr     |
| 19 | Cys—S—S— | Cys   |
| 20 | Gly     | Asn     |
| 21 | Glu     |         |
| 22 | Arg     |         |
| 23 | Gly     |         |
| 24 | Phe     |         |
| 25 | Phe     |         |
| 26 | Tyr     |         |
| 27 | Thr     |         |
| 28 | Pro     |         |
| 29 | Lys     |         |
| 30 | Thr     | Human Insulin |

For several years now a number of scientists have developed chemical methods to synthesize the two separate A and B peptide chains of insulin. When these two synthetic chains are mixed under proper conditions, the disulfide bridges are formed to give the active hormone but in very poor yield. This poor yield at the last step in the synthesis has been a stumbling block in developing a commercial synthesis of insulin. At the present time there is sufficient information at hand to develop good and practical synthesis of the A and B peptide chains. However, synthesis of either one of the chains is a lengthy and costly procedure. The fact that 90% or more of this synthetic effort is thrown away in the last step involving the condensation of the two chains has thwarted practical synthetis of human or any other insulin.

The biosynthesis of insulin takes place through a precursor molecule proinsulin in which the end of the B-chain is connected to the beginning of the A-chain through an intermediate connecting peptide chain (C-peptide) of about 33 amino acid residues. Actually proinsulin is a single peptide chain which is converted in the cell to insulin through enzymatic splitting of the C-peptide to yield the active molecule. In proinsulin the parts of the molecule which will utimately be the A and B chains are interconneced by disulfide bridges. The formation of these disulfide bridges takes place readily and specifically in the proinsulin molecule.

Although the animal cell finds it feasible to make insulin through the precursor, proinsulin, application of the same approach in the laboratory involves dumping about 35% of the synthetic effort at the last step. This is not attractive for an industrial synthesis process.

In greater detail, the biological synthesis of insulin occurs through a single peptide chain (proinsulin) in which the COOH-terminus of the B-chain is connected to the NH₂ - terminus of the A-chain through a peptide of about 33 amino acid residues. Whereas the disulfide bonds of the proinsulin can be reduced and then reoxidized to give the parent molecule in good yield (ca. 70%), similar treatment of the two chain insulin molecule results in a poor yield of reoxidized products containing the active insulin with correct pairing of disulfide bonds. This fact has handicapped chemical syntheses of insulin involving, as a last step, the combination of the two separate chains through formation of the disulfide bonds. The three-dimensional structure of insulin has revealed that the $NH_2$ — terminal glycine (designated A1) of the A-chain is located quite close (ca. 10A) to the epsilon amino of lysine (designated B29) which comprises the penultimate amino acid residue of the B-chain. Recently several investigators (D. G. Lindsay, FEB LETTS., V. 21, p.105, 1972; D. Brandenburg, W. D. Busse, H. G. Gattner, H. Zahn, A. Wollmer, J. Gleimann, and W. Puls in "Peptides: 1972", H. Hanson and H. D. Jukubke, Editors, North Holland Publ. Co., Amersterdam, Holland, P.270) have prepared intramolecularly cross-linked insulins involving linkage of the amino groups A1 to B29 through a series of dicarboxylic acids. In other studies, insulin derivatives which were crosslinked with suberoyl (—OC(CH$_2$)$_6$CO—) residues could be reduced and reoxidized to give good yields of products with the correct pairing of the disulfide bridges as judged by physical and chemical properties of the reoxidized products. (S. M. L. Robinson, I. Beetz, O. Loge, D. G. Lindsay and K. Lubke, Tetrahedron Letter. V. 12, p. 985 1973; D. Brandenburg, A. Wollmer, Hoppe-Seyler's Z. Physiol. Chem., V. 354, P. 613, 1973). However, the disadvantage of the proinsulin analogues is that the crosslinking residues cannot be removed. This disadvantage has been overcome by the use of the di(BOC) -α, α'-diaminosuberoyl residue. In that process, as reported by R. Geiger, R. Obermeier, Biochem. Biophys, Res. Commun. V, 55, p. 60, 1973 and D. Brandenburg, W. Schermutzki, H. Zahn, Hoppe-Seyler's Z. Physio. Chem. V. 354, p. 1521, 1973), after removal of the BOC-groups by trifluoracetic acid, the diamino-suberoyl moiety is removed by an Edman degradation but this involves a many step process and a further complication in that the Edman degradation also removes phenylalanine B1 so that the product is des Phe B1 insulin rather than insulin.

SUMMARY OF THE INVENTION

This invention presents a method for producing a proinsulin precursor wherein a reagent, for instance, carbonylbis (L-methionine p-nitrophenyl ester), cross-links the insulin A and B chains. The two chains which are cross-linked by the carbonyl-bis (methionyl) residue, hereinafter sometimes abbreviated as "CBM", undergo oxidative formulation of necessary disulfide links, followed by removal of the cross-linking reagent in a single one-step process to yield insulin. A method of preparing the cross-linking reagent is also disclosed.

In somewhat greater detail, the procedure involves interconnecting the two insulin peptide chains between the amino group on the A1 glycine residue on the A peptide chain and the epsilon amino group on the B29 lysine residue on the B peptide chain with the cross-linking reagent. Interconnecting the A and B peptide chains at these points facilitiates formation of the required disulfide cross-links between the A and B peptide chains. After formation of the disulfide bonds, the cross-linking reagent is removed in a one-step process without destroying the disulfide bonds to yield the desired insulin molecule.

More specifically, the A and B peptide chains are cross-linked with the reagent carbonyl-bis (L-methionine p-nitrophenyl ester) to yield a proinsulin-like precursor hereinafter termed "CBM proinsulin-like precursor". The CBM proinsulin-like precursor is then oxidized to form desired disulfide cross-links between the A and B peptide chains, thereby forming a proinsulin analogue, CBM insulin. The CBM insulin is then converted into insulin by cleaving off the carbonyl-bis (methionyl) cross-link to yield insulin. The cleavage is accomplished by a cynanogen bromide reaction that specifically splits peptide chains at methionine residues. The absence of methionine in insulin and the stability of insulin under the conditions of cyanogen bromide cleavage results in the formation of the desired insulin molecule.

It is therefore an object of the invention to provide a method for the final synthesis of insulin.

It is another object of the invention to provide a cross-linking reagent useful in the synthesis of insulin, isotopically labeled insulin and insulin analogues.

It is yet another object of the invention to provide a method for preparing the insulin cross-linking reagent.

Other advantages of the invention will become apparent from a review of the following description and claims appended hereto.

DETAILED DESCRIPTION OF THE INVENTION

The cross-linking reagents of the invention have the following general formula:

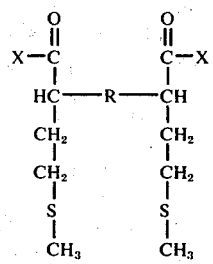

Thus the cross-linking reagents comprise a group R forming a connection between two 4-(methylthio) butyryl residues i.e.,

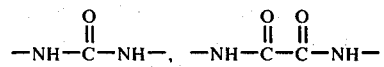

or, more generally,

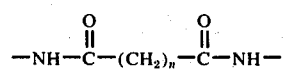

where $n$ is equal to or greater than zero; or in the broadest sense, —(CH$_2$)$_y$—, where y is equal to or greater than zero. The activated carbonyl radicals (X) one each of which is attached to the acyl carbons on the 4-(methylthio) butyryl residues may be an active ester, acid halogen or acid anhydride, such as, for instance,

nitrophenyl ester (either ortho-, meta-, or para-nitro);

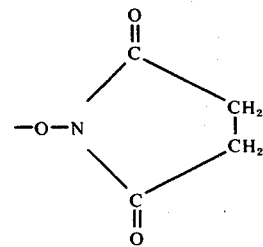

hydroxy succinimide; Cl, Br, or F; or acyloxy,

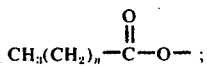

or aryl,

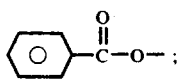

or branched acyloxy,

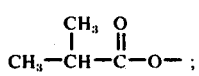

or mixed arylacyloxy,

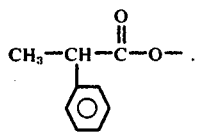

The preferred cross-linking reagent is carbonyl-bis (L-methionine p-nitrophenylester) that has the following formula:

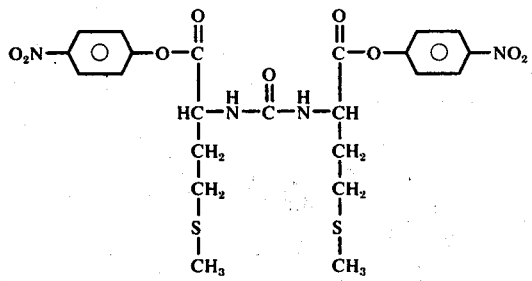

The preferred cross-linking reagent is prepared in good yield as follows:

L-methionine in 3N NaOH is reacted with 0.5 equiv. of phosgene in toluene at about 0° with vigorous stirring. Recrystallization from 15% acetic acid of the product obtained upon acidification of the reaction mixture gives carbonyl-bis (L-methionine) in 30–40% yield, m.p. 167°–180° $[\alpha]_D^{25}$ +4.8 (C, 1 methanol). The carbonyl-bis (L-methionine) is then reacted in dimethylformamide with two equiv. of dicyclohexylcarbodiimide and p-nitrophenol to yield the active ester, carbonyl-bis (L-methionine p-nitrophenyl ester) in 80% yield (after crystallization from tetrahydrofuran-ether), m.p. 183°–140°; $[\alpha]_D^{25} = -41°$ (c, 0.5, dimethylformamide).

The recovered cross-linking reagent has the ability to react with A and B insulin chains in their S-sulfonate forms to produce CBM proinsulin-like precursor in the S-sulfonate form. The S-sulfonates are reduced to give the CBM proinsulin-like precursor which is oxidized to give the CBM-insulin. The CBM reagent is removable from CBM-insulin in a single step reaction with cyanogen bromide (CNBr) to yield a true insulin molecule.

This ability to cross-link A and B insulin chains at the A1 glycine and B29 lysine positions and to be reversibly removed therefrom to yield insulin may be illustrated by the following Example 1:

EXAMPLE 1

Bovine insulin was reacted with 1 equiv. of CBM active ester in dimethyl sulfoxide in the presence of excess triethylamine at room temperature for 18 hr. The product was precipitated by methanol-ether and separated according to size by gel chromatography on Sephadex G-50 (fine) in 10% acetic acid to give a 70% yield of monomers which, after dialysis and lyophilization, were separated according to cationic charge on CM-cellulose in a solvent which was 7 M in acetic acid, and 0.075 M in NaCl. The fraction in the main peak, after dialysis and lyophilization, was separated according to anionic charge by chromatography on DEAE-cellulose at pH 7.2 in 0.01 M Tris, 0.09 M NaCl and 7 M urea. Dialysis followed by lyophilization of the main fraction gave CBM-insulin in overall yield of 30–40% from the starting insulin. The CBM-insulin product exhibited homegeneity of charge in cellulose acetate electrophoresis at pH 4.8 and of size in sodium dodecyl sulfate-gel electrophoresis. It had the correct amino acid composition including two methionines. The only free amino group as determined by the Edman or the dansyl method was present on phenylalanine. Only one peptide chain could be detected after oxidative sulfitolysis. In immunoassays by the double antibody technique, the CBM-insulin exhibited 90–92% of the activity of bovine insulin.

Recovered CBM-insulin (10 mg/ml) was reacted with CNBr (100 mg/ml) in 70% formic acid for 6 hr. The reaction mixture was diluted 10-fold with water and lyophilized. Chromatography of the product on DEAE-cellulose (vide supra) followed by dialysis and lyophilization of the material in the main peak gave insulin in 70–75% yield. The product was shown to be identical to insulin by crystallization of the zinc complex, by cellulose acetate and sodium dodecyl sulfate-gel electrophoresis, by amino acid composition, in circular dichroic spectrum, and in immunoassay. The above example demonstrates than an insulin derivative which is cross-linked between the amino groups of glycine A1 and lysine B29 with the carbonyl-bis (methionyl) residue is converted to insulin in good yield by the one step cyanogen bromide cleavage reaction.

The above sequence of reactions is as follows:

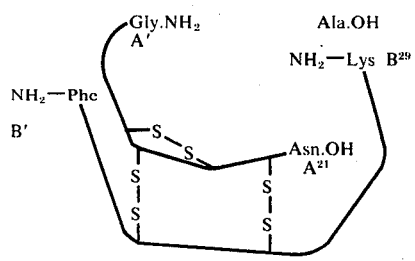

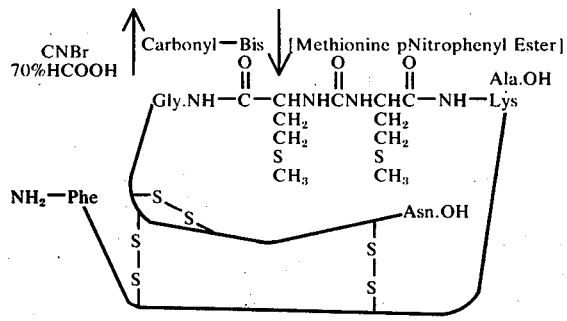

Of course, in the actual preparation of insulin from synthesized A and B peptide chains, it is not only necessary to spacially fix the chains by cross-linking at the preferred A1 glycine and B29 lysine positions, but, in addition, it is necessary to form the disulfide bridges present in a true insulin molecule. In the present instance, the disulfide bridges are simply formed on CBM proinsulin-like precursor when the precursor is oxidized in air.

Since synthetic A and B peptide chains are not readily available, the ability to form the disulfide bridges on CBM proinsulin-like precursor is shown by the following Example 2:

EXAMPLE 2

CBM-insulin (25 mg in 0.5 ml 0.1 M urea at pH 7.6) was treated with $Na_2SO_3$ (29 mg in 1 ml of Tris-Urea buffer) and $Na_2S_4O_6$, for 4 hr at room temperature. The reaction mixture was chromatographed on a column of Sephadex G-50 (fine) (2.5 × 150 cm) equilibrated and developed with 0.05 M $NH_4HCO_3$. The main protein peak, which eluted at $V_e$ of 390 ml for the starting CBM-insulin, was lyophilized to yield 22 mg (80%) of the S-sulfonated CBM-insulin. In three parallel experiments the latter compound (10 mg in 5 ml of 0.36 M Tris, 8 M urea, 0.25% EDTA at pH 8.6) was treated under nitrogen with dithiothreitol (15 mg) (DTT). After 1 hour at room temperature an aliquot (0.5 ml) was removed and subjected to carboxymethylation to demonstrate the complete reduction of the sulfhydryl form. The remaining solution was chromatographed on a Sephadex G-25 (fine) column (2.5 × 40 cm) which was equilibrated and developed with 0.05 M phosphate at pH 7.8. The material in the main protein peak ($V_e$ 85 ml) contained 5.5–5.8 sulfhydryls per mole of protein, as determined by the Ellman reagent. The eluate was diluted to give 0.1 mg of reduced protein per ml, and pH was adjusted to 9.5 and the solution contained in an Erlenmeyer flask coated with bovine serum albumin was stirred in air at room temperature for 10 hr. The reoxidation mixture was lyophilized and the residue chromatographed on a Sephadex G50 (fine) column (2.5 × 150 cm) which was equilibrated and developed with 0.5 M $NH_4HCO_3$. The material in the main peak ($V_e$ of 390 ml) was lyophilized to yield 6.8–7.8 mg (75–86%) of CBM-insulin which was shown to be identical to the starting material by cellulose acetate and sodium dodecylsulfate-gel electrophoresis, circular dichroic (CD) spectrum and immunoassay.

The above sequence of reactions is as follows:

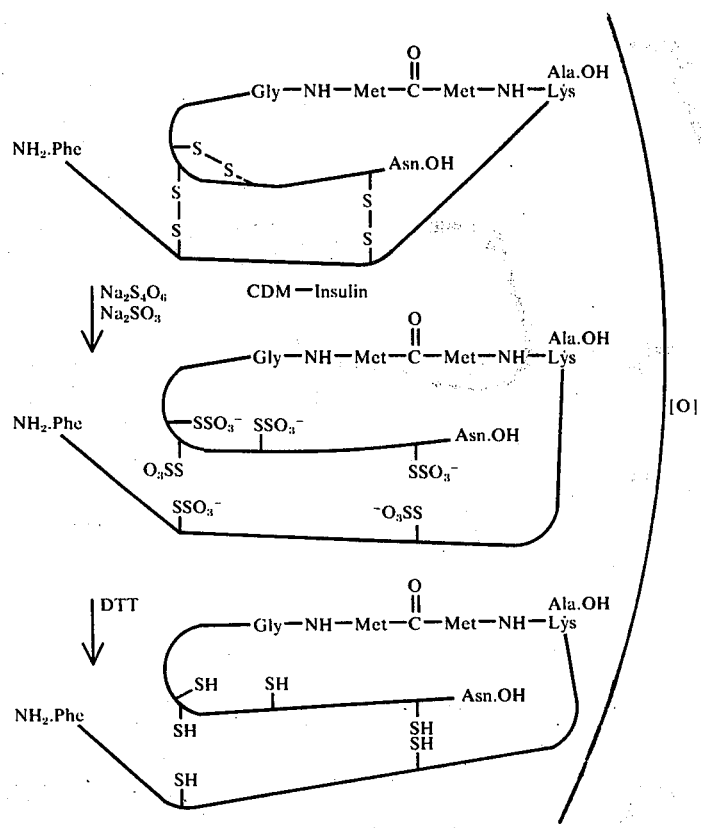

Example 2 demonstrates that the disulfide bridges on CBM-insulin may be completely degraded and thereafter reformed by simple air oxidation.

To further demonstrate that CBM-insulin, produced according to Example 2 is able to produce insulin by cleaving out the CBM with CNBr, CBM-insulin was treated in accordance with the following Example 3:

EXAMPLE 3

CBM-insulin (12.4 mg) which had been subjected to the reduction and reoxidation in accordance with Example 2 was treated with CNBr (344 mg) in 3 ml of 70% formic acid at room temperature for 18 hr. Insulin was isolated from the reaction mixture to give 8.4 mg (68%) of product which was identical to the native hormone in amino acid analysis, amino end groups and CD spectrum. The product yielded a crystalline zinc complex and gave the same fragmentation pattern as insulin on chymotrypsin digestion.

Example 3 unambiguously demonstrates that the correct pairing of disulfide bonds occurs during reoxidation of reduced CBM-insulin.

Insulin may be produced from synthesized A and B Peptide chains in accordance with the generalized series of reactions as follows:

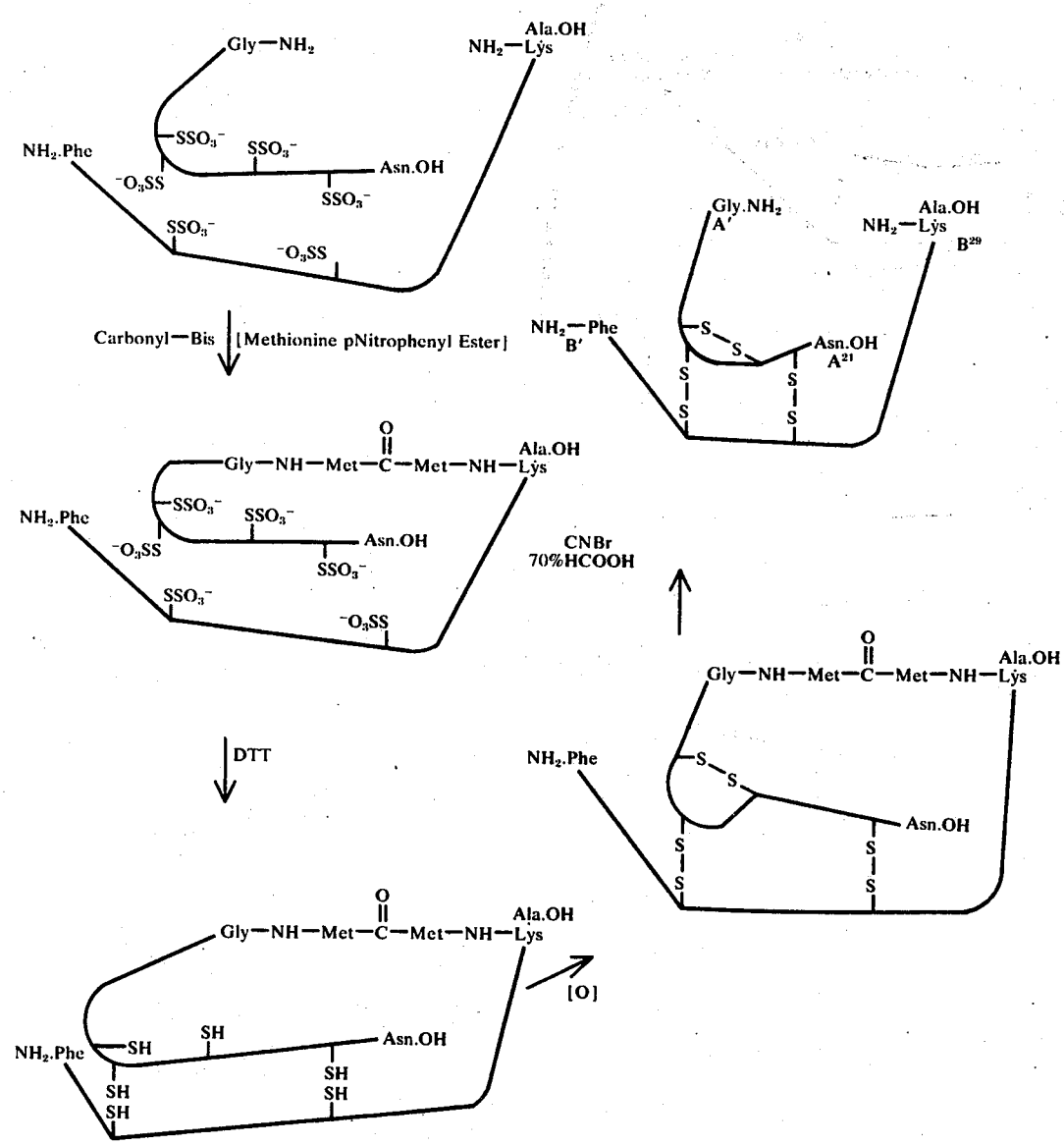

Thus the S-sulfonates of the A and B peptide chains are reacted with the CBM cross-linking reagent to produce CBM proinsulin-like precursor in the S-sulfonate form. The S-sulfonates of the proinslulin-like precursor are reduced to the sulfhydryl forms to give the CBM proinsulin-like precursor which is oxidized in air to give CBM-insulin. As a final step CBM is cleaved from the CBM insulin by the CNBr reaction, thereby yielding insulin.

CBM-insulin has further use in the degradation and resynthesis of insulin and insulin analogues that are modified at the NH₂ terminus of the B chain.

More specifically, proper diagnosis and treatment of diabetes mellitus requires a knowledge of the level of circulating insulin in the blood and other fluids. Assays are complicated by the fact that the level at which insulin occurs in the blood is in the order of a few nanograms per milliliter. However, assay of these insulin levels in the blood and other biological fluids can be performed by several radio-immunoassay techniques (C. N. Hales and P. J. Randle, Biochem, J., V. 88, P. 137, 1963). These techniques utilize a radioactive derivative of insulin. The derivative in current use is prepared by partial iodination of the tyrosines of insulin with radioactive iodine. Such derivatives have several shortcomings which has mediated against their routine use in clinical work. (1) The iodination reaction may inactivate the insulin to a variable degree, (2) the iodinated insulin is not identical to insulin and may not mimic the natural hormone in all of its properties, (3) the radioactive iodine has a short half-life (8 days for $^{131}$I) and consequently the radioactive derivative has a short-shelf life and must constantly be prepared anew.

The present invention provides a method whereby a radioactive insulin is prepared from CBM-insulin according to the reactions as follows:

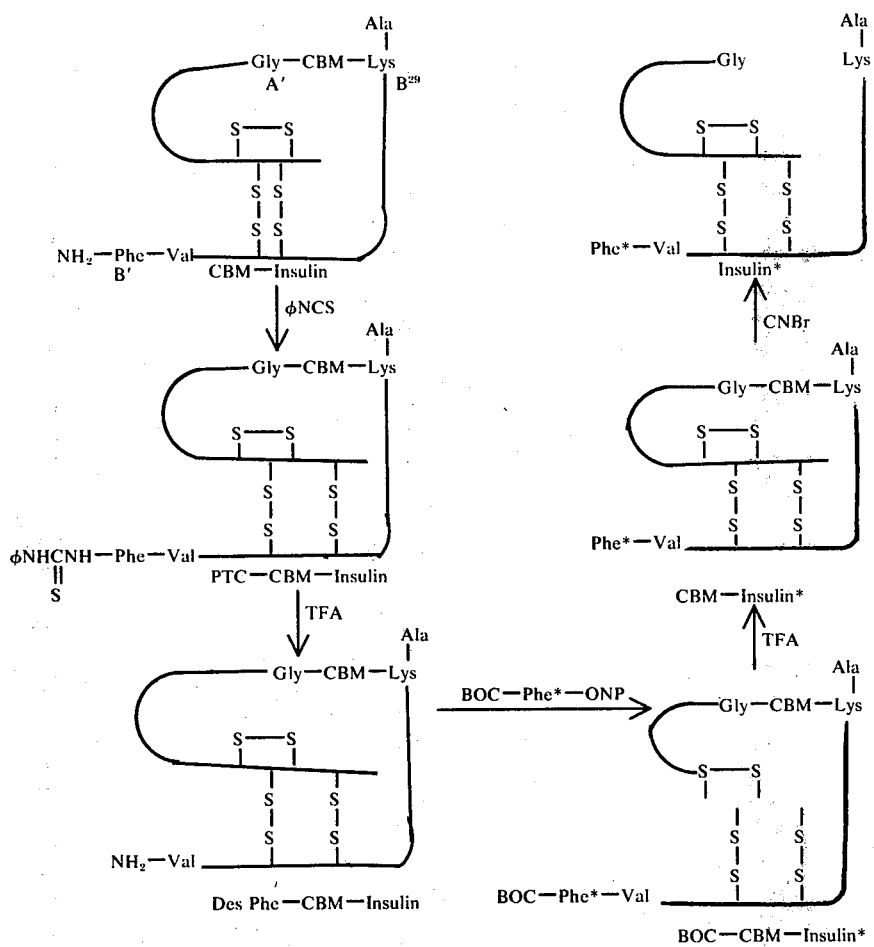

CBM-insulin is treated with phenylisothiocyanate (φNCS) to yield the phenylthiocarbamyl-derivative of CBM-insulin (PTC-CBM-insulin). The resulting derivative is treated with anhydrous TFA to remove the N-terminal amino acid residue and yield desphenylalanine-CBM-insulin (desPhe-CBN-insulin). This derivative is then treated with t-butyloxycarbonylphenylalanine p-nitrophenyl ester (BOC-Phe*-ONP) in which the phenylalanine moiety is radioactive. The latter is prepared from phenylalanine containing either $^{14}C$ or preferably $^{3}H$ or both. The product of the reaction is t-butyloxy-carbonyl-CBM-insulin* (BOC-CBM-insulin*) which contains a radioactive phenylalanine moiety. The BOC-group is removed by anhydrous trifluoroacetic acid to yield CBM-insulin* which in turn is treated with CNBr in 70% formic acid to remove the carbonyl-bis (methionyl) residue and to generate insulin* in which the NH₂ terminal phenylalanine on the B chain is radioactive.

The resulting product is superior to the iodinated derivative in that it is identical to the natural hormone in all of its biological properties and in that the radioactive label has a long half-life (5568 years for $^{14}C$; 12.4 years for $^{3}H$) which enables the derivatives to be stored for long periods before use. Such radioactive derivatives are useful not only for assay of insulin but in studies of insulin receptors on various tissue cells.

To illustrate the procedures involved in the degradation and resynthesis of insulin from CBM-insulin, a chemical labeled rather than a radioactive labeled insulin can be prepared. The chemical label may be the 2,4-dinitrophenyl residue which, when attached to an amino group, yields a brightly colored yellow compound. The reaction sequence is as follows:

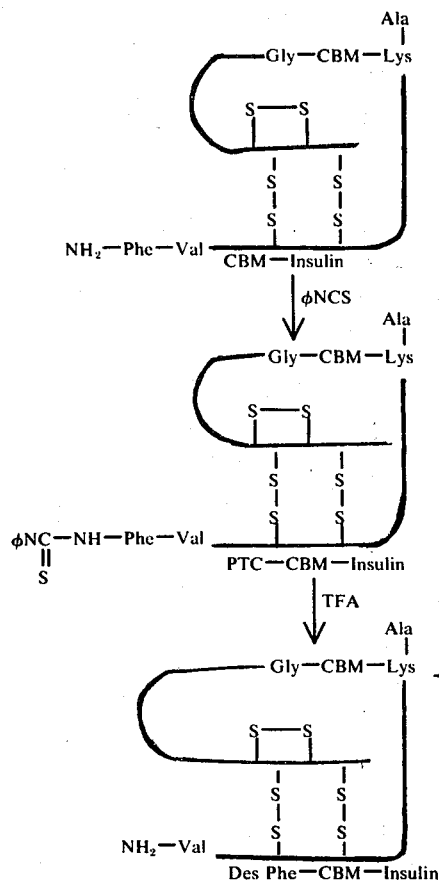

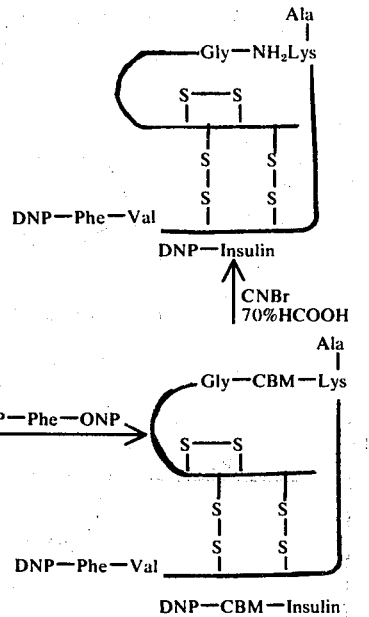

CBM-insulin is subjected to an Edman degradation under the conditions described above to yield des-Phe-CBM-insulin. The latter compound is treated with N-2,4-dinitrophenylphenylalanine p-nitrophenyl ester (DNP-Phe-ONp) to yield DNP-CBM-insulin. The carbonyl-bis (methionine) residue is then removed from the latter compound with CNBr in 70% formic acid to yield DNP-insulin. This reaction sequence in effect replaces the B1 phenylalanine of insulin with a chemically labeled phenylalanine in which the α-amino group of the phenylalanine carries the 2,4-dinitrophenyl residue. The above described reactions are more specifically described in the following Example 4:

EXAMPLE 4

CBM-insulin (140 mg) was dissolved in 2.5 ml 95% pyridine and 20 µl phenylisothiocyanate were added to the solution. Nitrogen was bubbled through the reaction mixture for 3 hr at room temperature. The protein (PTC-CBM-insulin), was precipitated by addition of 10 ml absolute ethyl ether, centrifuged, resuspended in ether and centrifuged (3×) to wash off pyridine and unreacted reagent.

Dry trifluoroacetic acid (TFA) (2.5 ml) was added and the precipitate went into solution. The reaction was carried out under $N_2$ for 1 hr at room temperature. The protein was again precipitated and washed with ether as in the first step. After desalting on a column of Sephadex G-25 in 10% acetic acid, dialysis against distilled water and lyophilization, 114 mg of Des-Phe-CBM-insulin were obtained. The amino acid analysis indicated the loss of exactly one Phe-residue per mole as compared with the starting CBM-insulin.

DNP-phenylalanine (3.31 g; 10 mmoles) was reacted with 1.39 g (10 mmoles) p-nitrophenol and 2.06 g (10 mmoles) dicyclohexyl carbodiimide (DCCI) in 40 ml redistilled dimethyl formamide for 24 hr at 2°–4°C. The dicyclohexyl urea was filtered, the DMF was removed under reduced pressure and the residue was dissolved in ethyl acetate, washed with 0.5 M $NH_4HCO_3$ and water. The ethyl acetate was removed after drying over $MgSO_4$ and the oily residue was recrystallized from tetrahydrofuran-ether, then isopropanol to yield, 1.85 g = 42%, MP: 130°, of N-dinitrophenyl-phenylalanine p-nitrophenyl ester (DNP-Phe-ONp).

Des-Phe-CBM-insulin (60 mg; 10 mmole) was reacted with a 10-fold excess of DNP-Phe-ONp (44.5 mg) in 2 ml DMF for 18 hr at room temperature. Five milliliters of 30% acetic acid were added to the reaction mixture and the resulting solution was chromatographed on Sephadex G-25 (2.5 × 35 cm), equilibrated with 30% acetic acid. The protein peak was pooled, and lyophilized to give DNP-CBM-insulin. To the protein, 2 ml of a solution containing 120 mg/ml CNBr in 70% formic acid were added and the reaction was carried out for 18 hr at room temperature. Water (20 ml) was added and the solution was freeze dried. The yellow protein (52 mg) was subjected to ion exchange chromatography on DEAE cellulose 2×40 cm) in a buffer containing 7 M urea, 0.01 M Tris, 0.09 M NaCl at a pH of 7.2. The main peak was pooled, acidified and dialyzed against distilled water and lyophilized to yield 24 mg of DNP-insulin.

The DNP-insulin is a useful reagent for locating the binding sites for insulin on the cell surface. DNP-insulin at physiological concentrations is allowed to bind to the cell. The resulting cell preparation is then treated with an antibody which is specific for the di-nitrophenyl residue (DNP-residue). The resulting cell-DNP-insulin-antibody complex is examined under the electron microscope.

Because of the large size of the antibody, its location on the cell surface can be visualized and from this the insulin receptor sites on the cell surface can be inferred.

What is claimed is:

1. A cross-linking reagent for use in peptide chains having the formula:

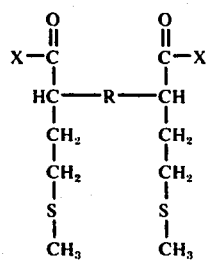

wherein R is selected from the group consisting of —(CH$_2$)$_n$—,

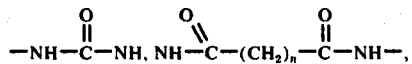

wherein $n$ is equal to or greater than zero; and wherein X is (selected from the group consisting of an active ester, an acid halide, and an acid anhydride) selected from the group consisting of ortho-, meta-, and para-nitrophenyl ester.

2. A reagent for use in cross-linking peptide chains, said reagent having the formula:

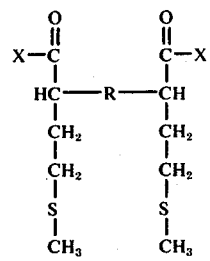

wherein R is selected from the group consisting of

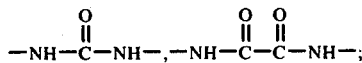

and wherein X is selected from the group consisting of ortho-, meta-, and para- nitrophenyl ester.

3. The cross-linking reagent carbonyl-bis (L-methionine p-nitrophenyl ester).

4. A method for producing the cross-linking reagent carbonyl-bis (L-methionine nitrophenyl ester) comprising reacting methionine with phosgene at a reduced temperature and in basic reaction medium, acidifying the reaction mixture to yield a crystalline product, separating the cyrstalline product, reacting the crystalline product with dicyclohexylcarbodiimide and nitrophenol to produce the cross-linking reagent.

* * * * *